US008636177B1

(12) United States Patent
Gardiner et al.

(10) Patent No.: US 8,636,177 B1
(45) Date of Patent: Jan. 28, 2014

(54) METHOD AND APPARATUS FOR DISPENSING SANITIZER FLUID

(75) Inventors: Virginia Gardiner, London (GB); Richard Gilbert, Henley-on-thames (GB); Damian Palin, Kells Village (IE); Jacob McKnight, Argyll (GB); Alexander R. Oshmyansky, Boston, MA (US)

(73) Assignee: Altitude Medical Inc., Boston, MA (US)

( * ) Notice: Subject to any disclaimer, the term of this patent is extended or adjusted under 35 U.S.C. 154(b) by 232 days.

(21) Appl. No.: 12/930,607

(22) Filed: Jan. 11, 2011

Related U.S. Application Data

(60) Provisional application No. 61/335,687, filed on Jan. 11, 2010.

(51) Int. Cl.
*B67D 1/07* (2006.01)
*A61L 2/00* (2006.01)

(52) U.S. Cl.
USPC ..................... 222/192; 222/181.3; 222/321.7; 422/292; 422/300

(58) Field of Classification Search
USPC ............ 222/192, 207, 402.1, 321.1, 321.7, 1, 222/180, 181.3; 422/292, 306, 123, 300
See application file for complete search history.

(56) References Cited

U.S. PATENT DOCUMENTS 3,967,478 A 7/1976 Guinn
4,046,508 A 9/1977 McDonald
4,710,634 A 12/1987 Brookes
4,896,144 A 1/1990 Bogstad
4,997,139 A * 3/1991 Menard .......................... 242/535
5,454,409 A 10/1995 McAffer et al.
5,808,553 A 9/1998 Cunningham
6,029,600 A * 2/2000 Davis ............................ 116/200
6,211,788 B1 4/2001 Lynn et al.
6,289,557 B1 * 9/2001 Manson et al. ................. 16/412
6,577,240 B2 6/2003 Armstrong
6,645,435 B2 11/2003 Dawson et al.
6,874,697 B2 4/2005 Callueng
7,080,427 B1 * 7/2006 Campopiano et al. ....... 16/110.1

(Continued)

FOREIGN PATENT DOCUMENTS

DE 198 57 268 A1 6/2000
WO WO 2007/107784 A2 9/2007

OTHER PUBLICATIONS

International Search Report and Written Opinion dated Nov. 12, 2008 for PCT Application No. PCT/US2008/006505.

(Continued)

*Primary Examiner* — Kevin P Shaver
*Assistant Examiner* — Stephanie E Williams
(74) *Attorney, Agent, or Firm* — Moser Taboada

(57) ABSTRACT

A method and apparatus for dispensing sanitizer fluid from a door handle, including a latch mechanism lever adapted for coupling to a door latch mechanism and a trigger lever coupled to the latch mechanism lever. The latch mechanism lever can be selectively actuated independent of the trigger lever to actuate the door latch mechanism without dispensing sanitizer fluid. The apparatus may further include a sanitizer fluid reservoir and a pump coupled to the trigger lever to control sanitizer fluid flow from the sanitizer fluid reservoir to a nozzle when the trigger lever is actuated, where the nozzle is positioned proximate the latch mechanism lever. Embodiments of the invention may further include a method of use of the apparatus.

11 Claims, 7 Drawing Sheets

(56) References Cited

U.S. PATENT DOCUMENTS

| | | | | |
|---|---|---|---|---|
| 7,320,418 | B2 * | 1/2008 | Sassoon | 222/649 |
| 7,338,646 | B2 * | 3/2008 | Gilbert | 422/292 |
| 2004/0223894 | A1 | 11/2004 | Gilbert | |
| 2006/0153733 | A1 | 7/2006 | Sassoon | |
| 2006/0245818 | A1 | 11/2006 | Stropkay et al. | |

OTHER PUBLICATIONS

International Preliminary Report on Patentability dated Dec. 17, 2009 for PCT Application No. PCT/US2008/006505.

Supplementary European Search Report mailed Jun. 6, 2011 for Application No. 087546180.0-2113/2155266 (PCT/U52008006505).

* cited by examiner

METHOD AND APPARATUS FOR DISPENSING SANITIZER FLUID

CROSS-REFERENCE TO RELATED APPLICATIONS

This application claims benefit of U.S. provisional patent application Ser. No. 61/335,687, filed Jan. 11, 2010, which is herein incorporated by reference.

BACKGROUND OF THE INVENTION

1. Field of the Invention

Embodiments of the present invention generally relate to health care technology and, particularly, to a method and apparatus for dispensing sanitizer fluid from a door handle.

2. Description of the Related Art

Prevention of harmful diseases is a major concern for governments as well as various enterprises, such as multi-national corporations. If these diseases are not contained, an epidemic may ensue resulting in widespread panic and disorder among the population. For example, health care facilities, such as hospitals, may be overrun with patients straining the available medical professional workforce. In order to ensure a productive work and living environment, various enterprises and governments use various health care technologies, such as a sanitizer fluid, to stop the spread of pathogens that cause the harmful diseases. Such sanitizer fluids are generally dispensed via pump canisters located in bathrooms or via wall mounted pump canisters distributed throughout a building. Such sanitizer availability may not be convenient nor does availability guarantee use of the sanitizer fluid.

Therefore, there is a need in the art for a method and apparatus for dispensing sanitizer fluid in a very convenient manner, via door handles such that sanitizer fluid is conveniently available throughout a building.

SUMMARY OF THE INVENTION

Embodiments of the present invention comprise a method and apparatus for dispensing sanitizer fluid from a door handle. One embodiment of the apparatus comprises a latch mechanism lever adapted for coupling to a door latch mechanism and a trigger lever coupled to the latch mechanism lever. The latch mechanism lever can be selectively actuated independent of the trigger lever to actuate the door latch mechanism without dispensing sanitizer fluid. The apparatus further comprises a sanitizer fluid reservoir and a pump coupled to the trigger lever to control sanitizer fluid flow from the sanitizer fluid reservoir to a nozzle when the trigger lever is actuated, where the nozzle is positioned proximate the latch mechanism lever. Embodiments of the invention further comprise a method of use of the apparatus.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
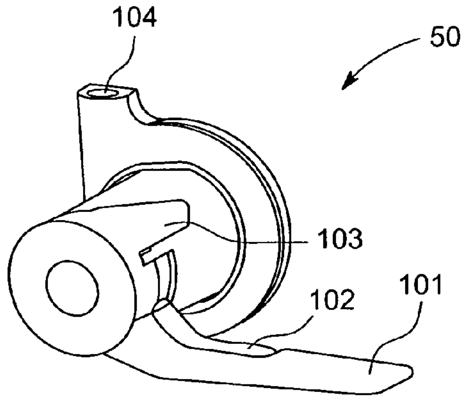
FIG. 1 depicts a perspective view of one embodiment of the present invention with the handle levers in a starting position.

FIG. 1 depicts a perspective view of a device (a handle 50) in accordance with one embodiment of the present invention comprising a latch mechanism lever 101 and a trigger lever 102, which are in a starting position. In the starting position, no mechanisms within the handle 50 are actuated and no sanitizer fluid is released through the nozzle 103. In one embodiment, a reservoir connection point 104 provides foaming sanitizer liquid to the device 50. Although foaming sanitizer liquid is described as used in one embodiment of the invention, other types of sanitizing fluids may be dispensed in various forms by the handle 50 including liquids, aerosols, sprays, streams and/or the like. All fluids based on or containing compounds with antibacterial, anti-viral, and/or anti-fungal properties could be used in the device, including but not limited to, ones based on: alcohol; benzochloronate; iodine; silver; silver-nitrate; TRIOSYN; and zinc, as well as combinations and compounds thereof. As described below, the device includes a handle or assembly that is used to unlatch and generally move a door (not shown).

Figure 2:
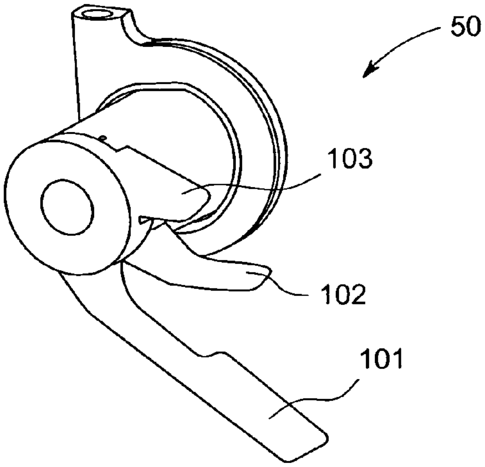
FIG. 2 depicts an embodiment of the present invention with a latch mechanism lever depressed (rotated)

FIG. 2 depicts the handle 50 with the latch-mechanism lever 101 depressed. As the latch mechanism lever 101 is rotated clockwise, a latch mechanism in a door is actuated by the movement of the handle spindle (not pictured). The independent rotation of a door latch mechanism 101 through a clockwise motion allows the door to be opened without sanitizer fluid being dispensed from the nozzle 103. This allows the user of the handle 50 to choose whether or not they wish to have the device dispense sanitizer by means of choosing to depress either the latch mechanism lever 101 alone, or the trigger lever 102 and the latch mechanism lever 101 combined. The placement of the nozzle 103 and the trigger lever 102 is 'prescriptive' in that if the user wishes the handle 50 to dispense sanitizer fluid, they must rotate the trigger lever 102 which places their hand directly beneath the nozzle 103. The system is returned to the starting position by means of the spring force of the door latch (not pictured) and the spring within the foaming pump 402.

Figure 3:
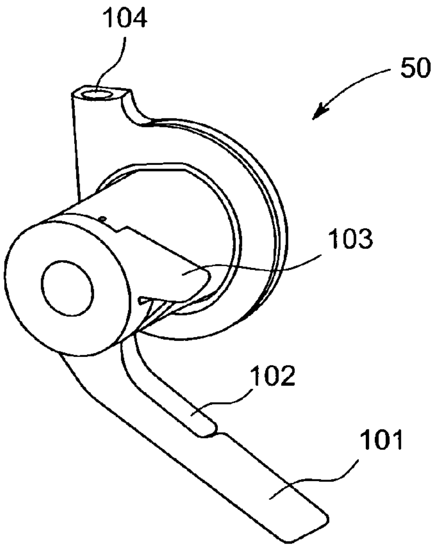
FIG. 3 depicts an embodiment of the present invention with both a latch mechanism handle lever and a pump trigger lever depressed (rotated)

FIG. 3 depicts the handle 50 with both the latch-mechanism lever 101 and the trigger lever 102 depressed. As the trigger lever 102 and the latch-mechanism lever 101 are rotated clockwise, a cam mechanism (not pictured) within a body of the handle 50 is actuated causing an internal pump (not pictured) to be depressed. As the pump is depressed, sanitizer fluid is dispersed through foaming elements of the internal pump to the nozzle 103. The nozzle deposits the sanitizer fluid or foam onto a hand that is actuating the handle 50. A reservoir couples with the handle 50 and provides a supply of foaming sanitizer fluid via a reservoir connection point 104.

Figure 4:
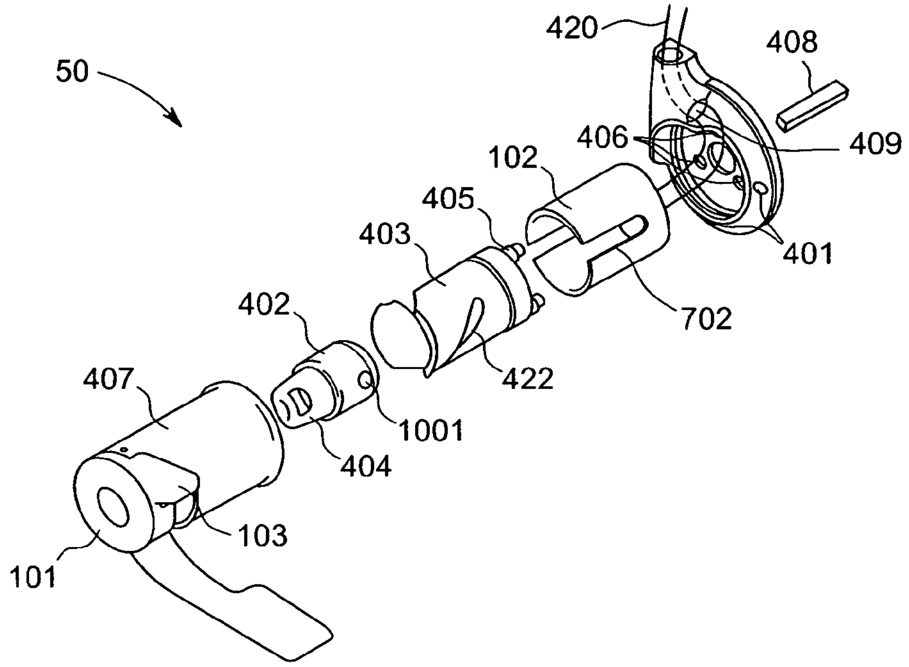
FIG. 4 depicts an exploded view of an embodiment of the present invention.
Figure 16:
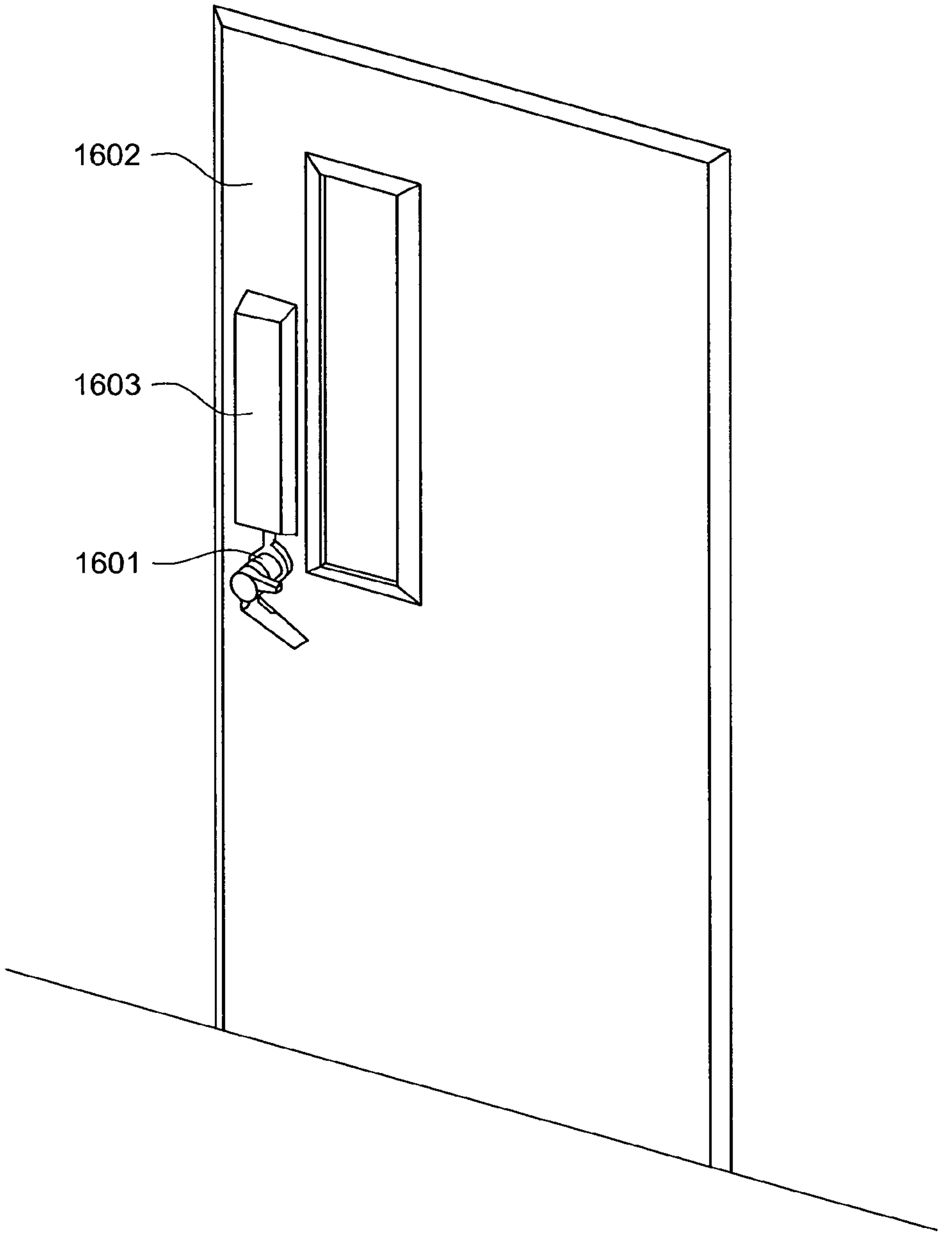
FIG. 16 depicts an embodiment of the handle and a reservoir that are fitted to a door.

FIG. 4 depicts an exploded view of the handle 50. A rear mount plate 410 is attached to a door (not shown) via bolts 401. The pump pin piece 402 fits within the helical slot cam 403 and holds a standard foaming pump 404. The helical slot cam 403 fits inside the trigger lever 102 and is attached to the rear mount plate 410 by three mounting pins 405 which fit into three mounting pin holes 406 whereas the trigger lever 102 is able to move freely. The trigger lever 102 is fitted into a handle sheath cylinder 407 which is fitted into the rear mount plate 410. The assembly is then enclosed by the latch mechanism lever 101 which fits over the handle sheath cylinder 407 and holds a handle spindle 408 which attaches to a conventional door latch mechanism within the door (not pictured). A reservoir, as described in the present disclosure with respect to FIG. 16, is connected to the foaming pump 404 via a plastic tube 420 routed through the connection port 409, through a routing hole 503 in the trigger lever 102, through the helical slot cam 403, which is fitted inside the body of the trigger lever 102 and into the foaming pump 404. As described in detail below, a pin 1001 interacts with a slot 422 in the helical slot cam 403 and a slot 702 in the trigger lever 102 to manipulate the pump 404.

Figure 5:
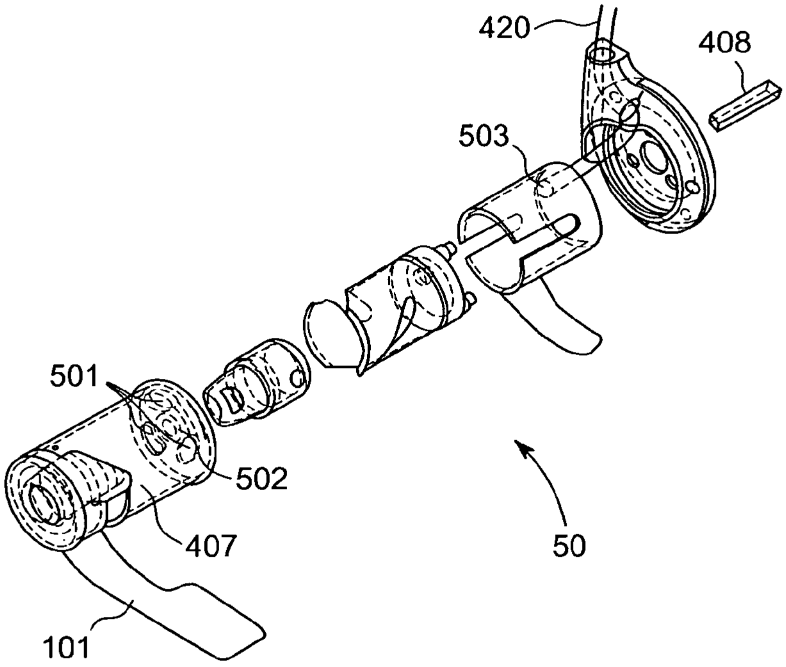
FIG. 5 depicts an exploded view of an embodiment of the present invention showing hidden lines.

FIG. 5 depicts an exploded view of the handle 50 with the hidden detail shown. The pin slots 501 in the handle sheath cylinder 407, allow the latch mechanism lever 101 and the handle sheath cylinder 407 assembly to rotate the spindle 408 which is held by a push fit into a cavity 502 in the handle sheath cylinder 407 causing the door latch (not pictured) to open without actuating the pump mechanism.

Figure 5A:
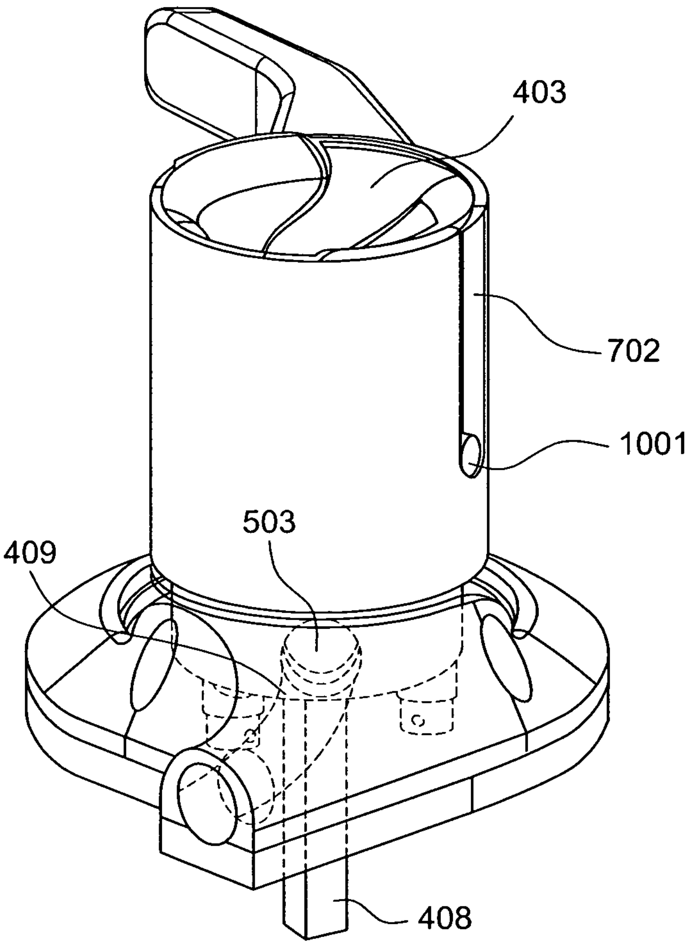
FIG. 5A depicts an embodiment of the present invention with the trigger lever attached to the rear mount plate.

FIG. 5A depicts an assembled view of the trigger lever 102, with the helical slot cam 403 disposed within, coupled to the rear mount plate 410. The connection port 409 leads to the routing hole 503 in the trigger lever 102.

Figure 6:
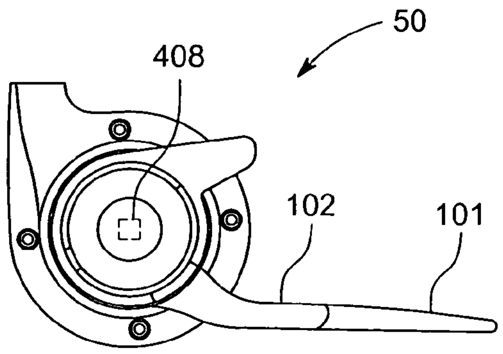
FIG. 6 depicts a front elevation view of an embodiment of the present invention with the handle levers in the starting position.

FIG. 6 depicts a front elevation view of the handle 50 with the trigger lever 102 and the latch mechanism lever 101 in the starting position. The spindle 408 is clearly in a similar orientation to the latch mechanism lever 101 and the trigger lever 102—square to the x and y axis.

Figure 7:
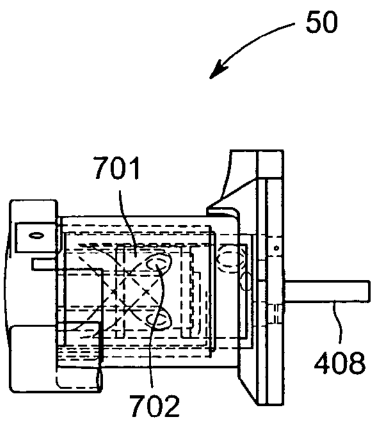
FIG. 7 depicts a side elevation view of an embodiment of the present invention with the handle levers in the starting position.

FIG. 7 depicts a side elevation view of the handle 50. Neither the top nor the underside of the spindle 408 is visible which illustrates the starting position. A slot 702 in the trigger lever piece 701 is unmoved suggesting that the internal cam mechanism assembly is also in the start position. Thus, the pump within remains fully uncompressed.

Figure 8:
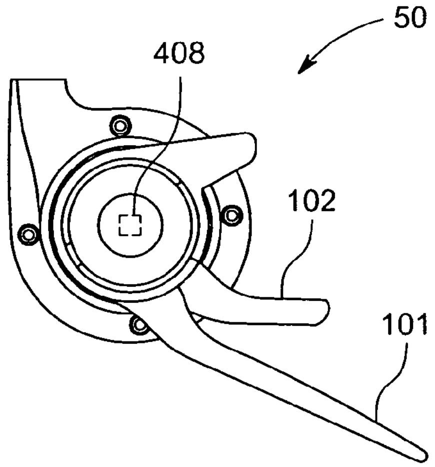
FIG. 8 depicts a front elevation view of an embodiment of the present invention with the latch mechanism lever in the depressed position.

FIG. 8 depicts a front elevation view of the handle 50 with the latch mechanism lever 101 in a depressed position and the trigger lever 102 in the starting position. The spindle 408 is clearly in a similar orientation to the latch mechanism lever 101 having been moved clockwise approximately 45 degrees by the movement of the latch mechanism lever 101. This movement of the spindle 408 actuates the latch mechanism within the door to which the handle 50 is mounted.

Figure 9:
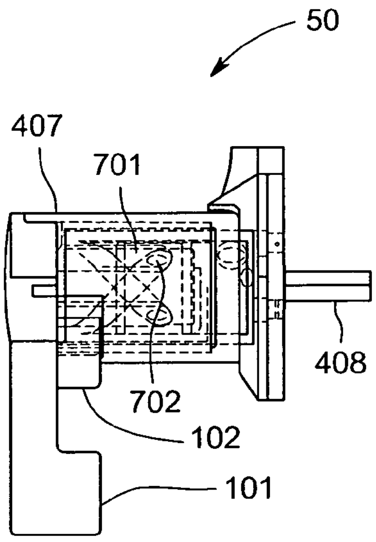
FIG. 9 depicts a side elevation view of an embodiment of the present invention with the latch mechanism lever in the depressed position.

FIG. 9 depicts a side elevation view of the handle 50 where the latch mechanism lever 101 is depressed. The handle sheath cylinder 407 and latch mechanism lever 101 has been rotated but the trigger lever 102 remains in the starting position. This has caused the spindle 408, which is fixed into the handle sheath cylinder 407, to rotate. The internal cam mechanism, however, is unaffected and remains in the start position as indicated by the non movement of the slot 702 in the trigger lever piece 701.

Figure 10:
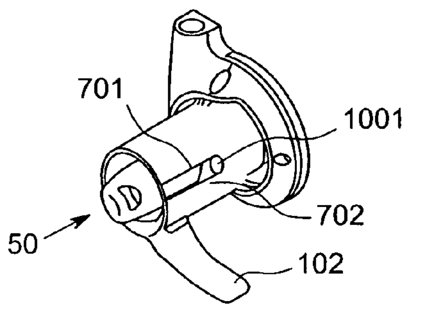
FIG. 10 depicts an embodiment of the present invention with the latch mechanism lever removed and the trigger lever in the starting position.

FIG. 10 depicts the handle 50 where the latch mechanism lever 101 is omitted and the trigger lever 102 is in the starting position. The pin 1001 is at the end of the visible slot 702 in the trigger lever piece 701.

Figure 11:
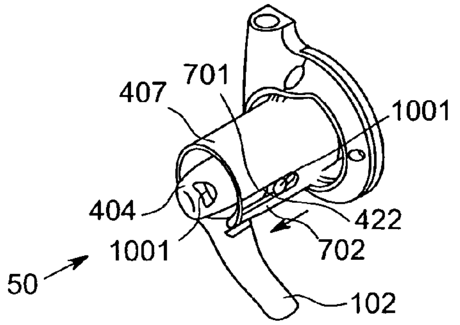
FIG. 11 depicts an embodiment of the present invention with the latch mechanism lever removed and the trigger lever in the depressed position.

FIG. 11 depicts the handle 50 without the latch mechanism lever 101 and where the trigger lever 102 is in a depressed position. As the trigger lever 102 is rotated clockwise, the edge of the slot 501 in the handle sheath cylinder 407 forces the pin 1001 to move along the slot 702 in the trigger lever 701 in direction Z (arrow). This motion causes the pin 1001 to move along the slot 422 in the helical cam slot piece 403 (FIG. 4). In moving along both of these slots 702 and 422, the force from the rotation of the trigger lever 102 is transformed into a lateral (linear) movement of the pump pin 1001 in direction Z. This movement forces the top surface of the pump 404 against the inside of the latch mechanism lever 101 which compresses the pump 404 forcing foamed sanitizer to exit the pump nozzle 1101 onto the hand. The pump nozzle 1101 fits within the latch mechanism lever 101 mould allowing the foamed sanitizer to flow from the pump 404 to the nozzle 103.

Figure 12:
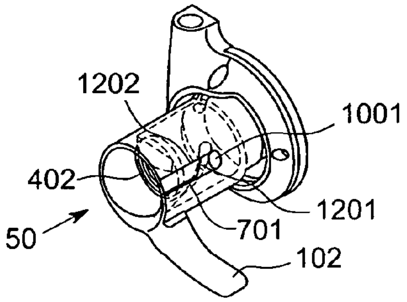
FIG. 12 depicts an embodiment of the present invention with the latch mechanism lever removed and the trigger lever in the starting position and with hidden lines made visible on the trigger lever and helical cam.

FIG. 12 depicts the handle 50 without the latch mechanism lever 101 and the pump 404 and where the trigger lever 102 in the starting position. The surface 1201 of the pump pin piece 402 is in the retracted position while the trigger lever 102 is in the starting position and the pin 1001 is at the end of the helical cam slot 1202 and the trigger lever slot 702.

Figure 13:
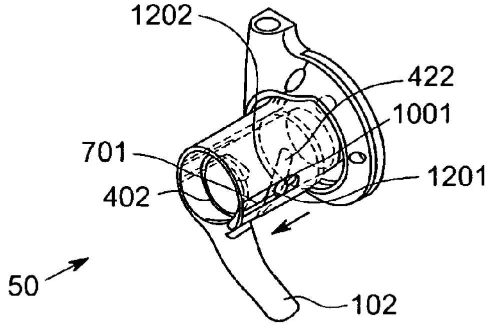
FIG. 13 depicts an embodiment of the present invention with the latch mechanism lever removed and the trigger lever in the depressed position and with hidden lines made visible on the trigger lever and the helical cam.

FIG. 13 depicts the handle 50 without the latch mechanism lever 101 and the pump 404. As the trigger lever 102 is moved into the depressed position, the surface of a pump pin piece 1201 can be seen to have been moved along axis Z as the pin 1001 has moved up the slot 422 in the helical cam slot piece 1202 and the trigger lever 701. This movement causes the pump 404 to be compressed and sanitizing foam to be forced from the pump 404.

Figure 14:
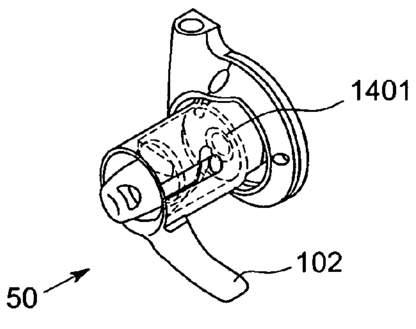
FIG. 14 depicts an embodiment of the present invention with the latch mechanism lever removed and the trigger lever in the starting position and with hidden lines made visible on the pump barrel.

FIG. 14 depicts the handle 50 without the latch mechanism lever 101 and where hidden detail is made visible and the trigger lever 102 is in the original position. Entry/exit point 1401 engages a tube (i.e., reservoir) (not shown) for carrying the sanitizing fluid.

Figure 15:
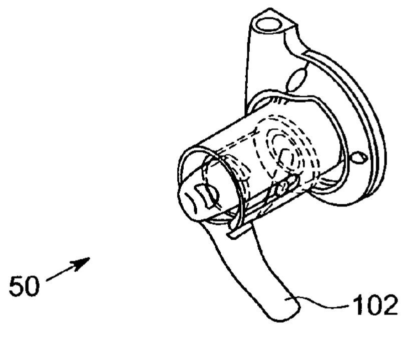
FIG. 15 depicts an embodiment of the present invention with the latch mechanism lever removed and the trigger lever in the depressed position and with hidden lines made visible on the pump barrel.

FIG. 15 depicts the handle 50 without the latch mechanism lever 101 and where the hidden detail is made visible and the trigger lever 102 is in the depressed position.

FIG. 16 depicts the handle 50 and a reservoir 1603 that are fitted to a door 1602. A connection sheath 1601 covers the tube 420 between the reservoir connection point 104 and the reservoir 1603. The reservoir fascia can be opened to allow a new cartridge to be fitted when the existing cartridge runs empty. In other embodiments, the tube may penetrate the door through a hole allowing the reservoir to be mounted on the opposite side of the door.

Figure 17:
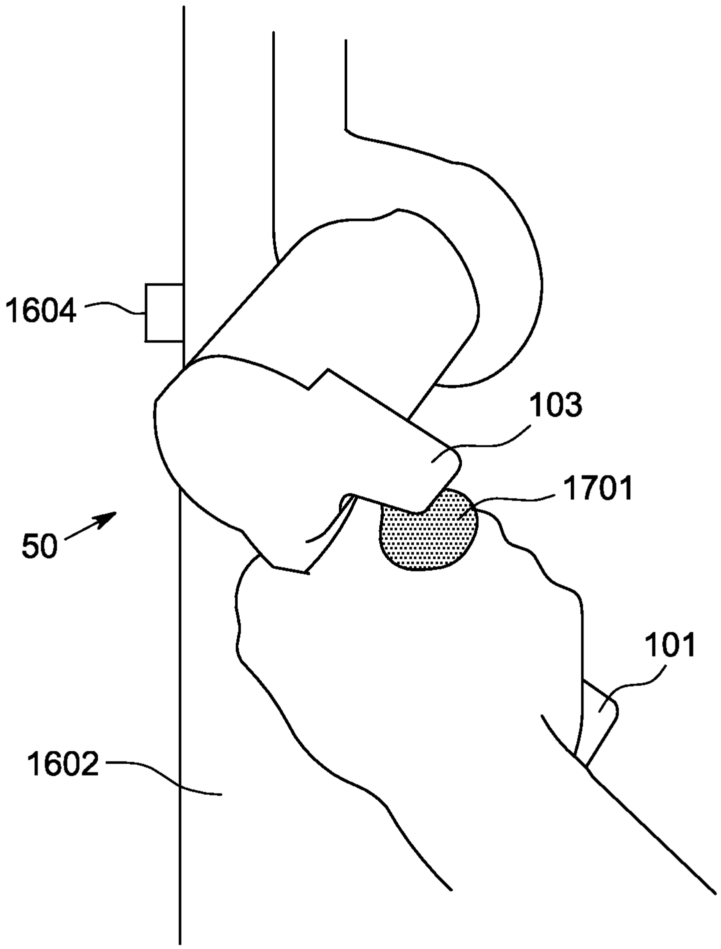
FIG. 17 depicts the handle in an unlatched position, while dispensing sanitizer onto the hand being used to turn the handle according to one or more embodiments of the present invention.

FIG. 17 depicts the handle 50 rotated to an unlatched position for a door 1602, while dispensing sanitizer fluid 1701 onto the hand being used to turn the handle 50 according to one or more embodiments of the present invention. The door 1602 comprises a door latch 1604, which is partially recessed into the door 1602 because the handle 50 is manipulated to open the door 1602. FIG. 17 further illustrates sanitizer fluid 1701 being released from nozzle 103.

While the foregoing is directed to embodiments of the present invention, other and further embodiments of the invention may be devised without departing from the basic scope thereof, and the scope thereof is determined by the claims that follow.

The invention claimed is:

1. An apparatus for dispensing sanitizer fluid comprising:

a latch mechanism lever adapted for coupling to a door latch mechanism;

a trigger lever coupled to the latch mechanism lever, where the latch mechanism lever can be selectively actuated independent of the trigger lever and the trigger lever is partially disposed within the latch mechanism lever;

a sanitizer fluid reservoir; and a pump coupled to the trigger lever to control sanitizer fluid flow from the sanitizer fluid reservoir to a nozzle when the trigger lever is actuated, where the nozzle is positioned proximate the latch mechanism lever and the trigger lever is coupled to a helical slot cam that interacts with a pump pin affixed to the pump, whereby rotational motion of the trigger lever is converted to linear motion to activate the pump.

2. The apparatus of claim 1 wherein rotation of the latch mechanism lever is adapted to manipulate a door latch and rotation of the trigger lever disperses sanitizer fluid.

3. The apparatus of claim 1 further comprising a resilient member for returning the latch mechanism lever and the trigger lever to a starting position after rotation.

4. The apparatus of claim 1, wherein an opening of the nozzle is oriented toward a surface of the latch mechanism lever.

5. The apparatus of claim 1 wherein the sanitizer fluid comprises: at least one of an antibacterial, anti-viral, or anti-fungal compound.

6. The apparatus of claim 1 wherein the sanitizer fluid is dispensed as a liquid, an aerosol, a spray, or a stream.

7. A method of selectively dispensing sanitizer fluid, comprising:

selectively manipulating a latch mechanism lever to manipulate a door latch, or the door latch mechanism lever and a trigger lever to manipulate a door latch and dispense sanitizer fluid proximate the latch mechanism handle, wherein the trigger lever is partially disposed within the latch mechanism lever and is coupled to a helical slot cam that interacts with a pump pin affixed to a pump.

8. The method of claim 7, wherein manipulating the trigger lever releases sanitizer fluid from a nozzle located proximate the latch mechanism assembly.

9. The method of claim 7 wherein manipulating the trigger lever actuates a pump for the sanitizer fluid.

10. The method of claim 7 wherein the sanitizer fluid comprises: at least one of an antibacterial, anti-viral, or anti-fungal compound.

11. The method of claim 7 wherein the sanitizer fluid is dispensed as a liquid, an aerosol, a spray, or a stream.

* * * * *